US005554371A

United States Patent [19]

Caputa et al.

[11] Patent Number: 5,554,371

[45] Date of Patent: Sep. 10, 1996

[54] RECOMBINANT VACCINE AGAINST LYME DISEASE

[75] Inventors: Anthony C. Caputa, Nanuet, N.Y.; Russell F. Bey, Arden Hills; Michael P. Murtaugh, Roseville, both of Minn.

[73] Assignee: Regents of the University of Minnesota, Minneapolis, Minn.

[21] Appl. No.: 227,478

[22] Filed: Apr. 14, 1994

Related U.S. Application Data

[63] Continuation of Ser. No. 790,332, Nov. 12, 1991, abandoned.

[51] Int. Cl.[6] .......................... A61K 39/00; A61K 39/02; C12P 21/00; C07K 16/00

[52] U.S. Cl. .................................... 424/234.1; 424/262.1; 424/184.1; 530/350; 530/388.2; 530/388.4; 435/69.1; 435/69.3

[58] Field of Search ............................ 424/184.1, 234.1, 424/262.1; 435/69.3, 69.1, 71.1

[56] References Cited

U.S. PATENT DOCUMENTS 4,721,617 1/1988 Johnson .................................... 424/92

FOREIGN PATENT DOCUMENTS 3942728 5/1991 Germany .
9109870 7/1991 WIPO .

OTHER PUBLICATIONS

Caputa Dissertation Abstracts International vol. 52/02–B Aug. 1991 Abstract only.
Caputa et al (Abstr.) Annual Meeting of Am. Soc for Microbiology May 1990 (Abst).
Anderson et al Annuls of the New York Academy of Sciences 539:181–191 1988.
A. G. Barbour et al., *J. Clin. Invest.*, 72, 504 (1983).
S. Bergstrom, *Mol. Microbiology*, 4, 479 (1989).
R. Bey et al., *Infect. Immunol.*, 19, 562 (1978).
M. Bradford, *Anal. Biochem.*, 72, 248 (1976).
W. Burgdorfer et al., *Science*, 216, 1317 (1982).
I. Charles et al., *PNAS USA*, 86, 3554 (1989).
C. Collins et al., *Infect. Immunol.*, 59, 519 (1991).
J. Craft et al., *J. Infect. Dis.*, 149, 789 (1984).
E. Engvall et al., *Immunochemistry*, 8, 871 (1971).
E. Fikrig et al., *Science*, 250, 553 (1990).
L. Guo et al., *Gene*, 29, 251 (1984).
R. Grodzicki et al., *J. Infect. Dis.*, 157, 790 (1988).
K. Hansen et al., *Infect. Immunol.*, 56, 2047 (1988).
T. R. Howe et al., *Infect. Immunol.*, 54, 207 (1985).
R. Johnson et al., *Infect. Immunol.*, 53, 713 (1986).
R. Johnson et al., *Infect. Immunol.*, 54, 897 (1986).
U. Laemmli et al., *Nature*, 227, 680 (1970).
K. Loken et al., *Proc. Soc. Exp. Biol. Med.*, 179, 300 (1985).
L. Magnarelli et al., *J. Clin. Microbiol.*, 20, 181 (1984).
L. Magnarelli et al. *J. Infect. Dis.*, 156, 183 (1987).
H. Russell et al., *J. Infect. Dis.*, 149, 465 (1984).
J. L. Schmidtz et al., *Infect. Immunol.*, 58, 144 (1990).
R. Wallich et al. *Infect. Immun.*, 58, 1711 (1990).
R. Young et al., *PNAS USA*, 80, 1194 (1983).
Philipp et al Inf & Immun. 61:3047–3059 1993 Early & Early Disseminated Phases of Lyme Disease in the Rhesus Monkey: A Model for Infection in Humans.
Fikrig et al I & I 60:773–777 1992.
Fikrig et al I & I 61:2553–2557, 1993.
Label for *Borrelia burdorferi* Bacterin, Fort Dodge Laboratories, Inc. (Sep. 7, 1990).
Szczepavski et al Microbiological Reviews 55:21–43 1991.
Edelman, Vaccine 9:531–532 1990.
Kanfor Scientific American Sep. 1994, pp. 34–39.
Caputa Dissertation, Abstract & pages.
Caputa ASM Abstract 1990.
Caputa et al, The Journal of Clinical Microbiology 29:2418–2423, 1991.
Schaible et al PNAS 84:3768–3772 1990.

*Primary Examiner*—Hazel F. Sidberry
*Attorney, Agent, or Firm*—Schwegman, Lundberg, Woessner & Kluth P.A.

[57] ABSTRACT

A highly-antigenic, recombinant polypeptide of a molecular weight of about 110-kD by SDS-PAGE is disclosed, which is derived by transforming *E. coli* with a 7.1 kB DNA fragment from EcoR1-digested *B. burgdorferi* DNA, followed by identification of cloned transformants expressing polypeptides which bind to anti-*B. burgdorferi* antibodies.

8 Claims, No Drawings

RECOMBINANT VACCINE AGAINST LYME DISEASE

This is a continuation of application Ser. No. 07/790,332, filed Nov. 12, 1991, now abandoned.

BACKGROUND OF THE INVENTION

The genus *Borrelia* is included in the order *Spirochaetales* ("spirochetes") and family *Spirochaetaceae. Borrelia* species are associated with arthropod hosts and often have limited geographical ranges. Lyme borreliosis, a systemic illness with a wide spectrum of clinical symptoms, was named for Lyme, Conn., where the disease was recognized and studied in 1975.

The illness usually develops 3 to 30 days following the bite of an ixodid tick which transmits *Borrelia burgdorferi* to humans and animals. The disease in humans often begins with a primary skin lesion called erythema migrans (EM) which may be followed by cardiac, neurologic, or arthritic symptoms. The primary clinical sign in dogs and horses is lameness.

Antigenic proteins can be isolated from *B. burgdorferi* by immunoprecipitation, extraction from SDS polyacrylamide gels, or by molecular cloning and expression. The first two methods require large numbers of organisms, creating a logistical problem with *B. burgdorferi,* which has a generation time of 8 to 24 hours at 32° C. and reaches a maximum cell density of $10^7$ to $10^8$ cells/ml.

Molecular cloning of protein antigens in a host such as *Escherichia coli* can result in their production in large amounts without contamination by other spirochete antigens. Using *E. coli* as a host for molecular cloning also avoids association of *B. burgdorferi* antigens with rabbit serum since the *E. coli* can be grown in Luria broth (LB) containing no rabbit serum. This is critical in the development of vaccines since spirochetal antigens may adsorb rabbit serum, a component of the medium used to propagate *B. burgdorferi,* potentially resulting in anaphylactic shock when administered to animals including humans.

Two major surface proteins with molecular weights of 31 kilodalton (-kD) and 34-kD (OspA and OspB, respectively) have been cloned, sequenced, and characterized. See, S. Bergstrom et al., *Mol. Microbiol.,* 4, 479 (1989). Those two proteins are under the control of a single promoter and are found on a linear plasmid. See, T. R. Howe et al., *Infect. Immunol.,* 54, 207 (1985).

The 41-kD protein, a flagellin component, has been cloned, sequenced and found to be recognized early in the immune response by A. G. Barbour et al., *J. Clin. Invest.,* 72, 504 (1983) and R. Wallech et al., *Infect. Immun.,* 58, 1711 (1990). Unfortunately, human antibodies specific to this flagellin component cross react with other species of *Borrelia,* thus reducing the specificity of potential serological assays for the diagnosis of Lyme disease which use the flagellin protein as the "capture antigen". C. Collins et al., *Infect. Immunol.,* 59, 519 (1991).

A fourth immunodominant protein also has been cloned by K. Hansen et al., *Infect. Immunol.,* 56, 2047 (1988). Antibodies to this 60-kD recombinant protein also cross reacts with a large variety of microorganisms including *Pseudomonas* and *Legionella,* therefore this antigen is not useful for diagnosis of Lyme borreliosis.

Recently, W. J. Simpson et al., *J. Clin. Microbiol.,* reported cloning a 6.3 Kb EcoR1 chromosomal fragment of *B. burgdorferi* DNA, which encoded two proteins of 28-kD and 39-kD. These two antigens were reported to be immunologically distinct from OspA, OspB and the 41-kD flagellin protein.

Progress towards prevention and treatment of Lyme borreliosis in humans and domestic animals has been aided by the development of laboratory animal models exhibiting signs of Lyme borreliosis. Rabbits and guinea pigs develop skin lesions resembling human EM lesions but no other signs of disease. Hamsters develop arthritis when inoculated in the paw and are irradiated. Infant and weanling laboratory rats develop a persistent multisystemic infection, polyarthritis, and carditis after intraperitoneal (i.p.) inoculation of *B. burgdorferi.* Mice (C3H/He) develop spirochetemia, carditis, and polyarthritis after interperitoneal (i.p.) inoculation of *B. burgdorferi.* The last two animal models closely mimic human Lyme borreliosis.

With the development of laboratory animal models which have signs of Lyme borreliosis, research is in progress to determine if they can be protected from experimental *B. burgdorferi* infection and/or clinical manifestations of disease. The ability to protect laboratory animals from *B. burgdorferi* infection was first demonstrated by Johnson et al., *Infect. Immunol.,* 54, 897 (1986) who showed that hamsters were protected from infection by immunization with formalin treated *B. burgdorferi* spirochetes. The hamsters were also protected by the administration of sera obtained from rabbits immunized with the spirochetes. (R. C. Johnson et al., *Infect. Immunol.,* 53, 713 (1986)). At thirty days postvaccination with spirochetes, 86–100% protection against infection was exhibited by hamsters receiving 50 and 100 mg (dry weight) of this vaccine. However, resistance to infection decreased to 25% and 40% for the 100 mg and 50 mg vaccine doses, respectively, at 90 days post-vaccination.

Protection from infection and induction of Lyme arthritis also was shown in irradiated hamsters by the injection of *B. burgdorferi* and immune serum in the hind paw by J. L. Schmidtz et al., *Infect. Immunol.,* 58, 144 (1990). Recently, Fikrig et al., in *Science,* 250, 553 (1990), reported that C3H/He laboratory mice were protected from infection and induction of Lyme arthritis by active immunization with the purified recombinant OspA protein.

Vaccines based on recombinant polypeptides have a number of potential advantages over vaccines based on the "killed" or inactivated parent organisms, including lack of infectivity and side effects, reproducibility and high antigenicity. Therefore a need exists for recombinant vaccines which are effective to protect mammals against *B. burgdorferi* infection (Lyme disease) for prolonged periods of time, while exhibiting minimal host toxicity.

SUMMARY OF THE INVENTION

The present invention provides a highly-antigenic, recombinant polypeptide of a molecular weight of about 110 kD by SDS-PAGE (sodium dodecylsulfate-polyacrylamide gel electrophoresis) wherein the amino acid sequence of the polypeptide corresponds to the amino acid sequence of the recombinant 110-kD protein produced by *E. coli* transformant ATCC 68825. The present invention also provides a vaccine comprising this polypeptide as the immunogenic active ingredient, wherein the polypeptide is combined with a physiologically-acceptable, non-toxic liquid vehicle. This vaccine is effective to actively immunize a susceptible mammal, such as a human, dog, cat, sheep, goat, bovine, llama, or horse, against Lyme borreliosis.

The immunogenic amount of the recombinant 110-kD protein is typically suspended or dissolved in the physiologically-acceptable, non-toxic liquid vehicle, preferably with one or more conventional vaccine adjuvants, to yield an injectable or an orally ingestible vaccine. For example, vaccination of mice with a single dose of about 20 μg of the purified 110-kD polypeptide in Freunds complete adjuvant can provide effective protection against infection due to a subsequent *B. burgdorferi* challenge.

As used herein, the term "recombinant" is intended to mean that the 110-kD polypeptide (or "protein") is obtained by the techniques of genetic engineering from a microorganism, such as a bacterial cell, which has been transformed using an appropriate vector with foreign DNA fragments obtained from the genome of a strain of *B. burgdorferi.* Thus, the present 110-kD polypeptide has an amino acid sequence that corresponds essentially to that of the 110-kD polypeptide obtained by *E. coli* transformant designated A-1-24 herein and deposited in the American Type Culture Collection, Rockville, Md., USA, under accession number ATCC 68825. However, as used herein, with respect to the "foreign" DNA fragments useful in the present invention, the term "obtained from the genome of *B. burgdorferi*" is intended to encompass DNA extracted directly from the spirochetes, as well as totally-or partially-synthetic DNA sequences based upon sequenced portions of the *B. burgdorferi* genome, that encode said 110-kD protein, or an antigenically-active subunit thereof that is also reactive with Lyme borreliosis serum and that can function as a vaccine, such as the 75-kD *B. burgdorferi* polypeptide discussed hereinbelow.

Although the sequence of the 110-kD polypeptide antigen is unknown, as is the sequence of the 7.1 kilobase (Kb) DNA fragment from *B. burgdorferi* that encodes it, the polypeptide has been extensively characterized, as described hereinbelow. The 110-kD polypeptide is antigenically distinct from OspA (31-kD), OspB (34-kD), the 41-kD flagellin protein or the 60-kD or 68-kD proteins discussed hereinabove, or any known subunit proteins derived therefrom. The 110-kD polypeptide can be referred to as "essentially pure," in that it is not in association with any of the other polypeptides or proteins of *B. burgdorferi.*

During infection with *B. burgdorferi,* mammals develop an antibody response to the 110-kD polypeptide that does not develop during the course of infection with other spirochetes. Cross-reaction of anti-110-kD sera with other spirochetes was minimal, and hybridization of the DNA encoding the 110-kD protein to DNA from other *Borrelia* species was not observed. Thus, the present recombinant 110-kD polypeptide is useful as the "capture antigen" to detect anti-*B. burgdorferi* antibodies in a mammalian physiological fluid such as blood, lymph or cerebrospinal fluid (CSF). Formats for this type of assay are well known, and are exemplified hereinbelow. Thus, an assay for *B. burgdorferi* infection or for Lyme disease using the 110-kD polypeptide to detect antibodies against *B. burgdorferi* is also within the scope of the invention, as is a kit for conducting the assay. The kit can comprise a separately-packaged amount of the immobilized 110-kD polypeptide of the invention, a separately-packaged amount of the labelled detection antibody, and, optionally, a separately-packaged amount of an indicator such as a substrate for an enzyme label bound to the detection antibody, along with printed or recorded instructions for carrying out the present assay.

Polyclonal antibodies raised against the 110-kD antigen reduced the concentration of *B. burgdorferi* spirochetes in vitro and protected mice from joint swelling following a challenge with *B. burgdorferi.* Mice immunized with purified recombinant 110-kD polypeptide, challenged with *B. burgdorferi* and sacrificed at 14 days show no evidence of Lyme disease, or of infection. Thus, monoclonal or polyclonal antibodies which bind to the 110-kD polypeptide, while not significantly cross-reacting with other *B. burgdorferi* polypeptides or proteins are also within the scope of the invention.

As used herein with respect to molecular weight the term "about" is intended to encompass the inherent error present in estimating the molecular weights of proteins from bands on polyacrylamide gels, using internal standards, by methods described in detail below. Such error results in a variation of no more than about ±10-kD, preferably no more than about ±5-kD.

DETAILED DESCRIPTION OF THE INVENTION

This invention relates, in part, to recombinant *Borrelia burgdorferi* antigenic polypeptides and their encoding DNA. A principle embodiment of this aspect of the present invention relates to an antigenic protein, characterized by a molecular weight of about 110-kD as determined by SDS-PAGE and reactivity with human Lyme borreliosis serum. The present invention also relates to a unique portion of the above polypeptide or of the DNA sequence that encodes it, wherein the unique portion consists of at least 5–6 amino acids, or at least 7 nucleotide bases, respectively.

The 110-kD polypeptide is substantially free of proteins with which it is normally associated in the spirochete.

The present invention also relates to a DNA fragment encoding all, or a unique antigenic portion, of the 110-kD protein of the present invention. A principle embodiment of this aspect of the invention relates to the 7.1 kilobase (Kb) pair EcoR1 fragment obtained from a DNA library of *B. burgdorferi* DNA which encodes the 110-kD antigenic polypeptide.

The present invention further relates to antibodies specific for the 110-kD polypeptide of the present invention. One skilled in the art using standard methodology can raise monoclonal antibodies and polyclonal antibodies to the 110-kD polypeptide, or an antigenic portion thereof. This is exemplified by anti-110-kD polypeptide rabbit and mouse antisera.

The present invention also relates to a vaccine for use in mammals against Lyme borreliosis disease. In one embodiment of this aspect of this invention, as is customary for vaccines, the 110-kD polypeptide of the present invention can be delivered to a mammal in a pharmacologically acceptable vehicle. As one skilled in the art will understand, it is not necessary to use the entire protein. A unique portion of the polypeptide (for example, a synthetic polypeptide corresponding to a portion of the 110-kD polypeptide can be used. Vaccines of the present invention can include effective amounts of immunological adjuvants known to enhance an immune response. The polypeptide is present in the vaccine in an amount sufficient to induce an immune response against the antigenic polypeptide and thus to protect against Lyme borreliosis infection. Protective antibodies are usually best elicited by a series of 2–3 doses given about 2 to 3 weeks apart. The series can be repeated when circulating antibodies concentration in the patient drops.

The present invention further relates to diagnostic assays for use in human and veterinary medicine. For diagnosis of Lyme borreliosis disease, the presence of antibodies to the 110-kD polypeptide protein or the presence of the corresponding "native" 75 kD protein in mammalian serum is determined. Many types of test formats, as one skilled in the art will recognize, can be used. Such tests include, but are not limited to, IFA, RIA, RIST, ELISA, agglulination and hemagglutination. The diagnostic assays can be performed using standard protocols such as those described by Magnarelli et al., *J. Clin. Microbiol.*, 20, 81 (1984); Craft et al., *J. Infect. Dis.*, 149, 789 (1984); Enguall et al., *Immunochemistry*, 8, 871 (1971); and Russell et al., *J. Infect. Dis.*, 149, 465 (1984).

Specifically, a diagnostic assay of the present invention can be constructed by coating on a surface (i.e., a solid support) for example, a plastic bead, a microtitration plate or a membrane (e.g., nitrocellulose membrane)., all or a unique portion of the 110-kD polypeptide (natural or synthetic) and contacting it with the serum or other physiological fluid taken from a patient suspected of having a *B. burgdorferi* infection or Lyme borreliosis disease. Following removal of the physiological fluid, any antibody bound to the immobilized 110-kD polypeptide (the antigen) can be detected, preferably by reacting the binary antibody-antigen complexes with a "detection antibody" such as a (goat-, sheep- or rabbit-) anti-human IgG, which detection antibody comprises a detectable label or a binding site for a detectable label. Suitable detectable labels are enzymes, fluorescent labels or radiolabels. For example, the ternary complex comprising the 110-kD polypeptide, the *B. burgdorferi* antibody and a detection antibody having an enzyme label can be detected by reaction of the enzyme with its substrate.

In another embodiment of the diagnostic assay of the present invention, all or a unique portion of the 110-kD polypeptide is bound to an inert particle of, for example, bentonite, polystyrene or latex. The particles are mixed with serum from a patient in, for example, a well of a plastic agglutination tray. The presence or absence of antibodies in the patient's serum is determined by observing the settling pattern of the particles in the well.

In a further embodiment of the diagnostic assay of the present invention, the presence or absence of the corresponding 75 kD protein in a serum sample is detected. Antibodies specific for the 110-kD polypeptide or a unique antigenic portion thereof can he coated onto a solid surface such as a plastic and contacted with the serum sample. After washing, the presence or absence of the protein from the serum bound to the fixed antibodies is detected by addition of a labeled (e.g., fluorescently labeled) antibody specific for the 75 kD protein or the 110-kD polypeptide.

One skilled in the art will appreciate that the invention includes the use of competition-type assays in detecting in a sample the antigens and antibodies to which this invention relates.

The present invention is based upon the isolation of cloned *E. coli* transformant expressing a 110-kD *B. burgdorferi* polypeptide antigen. To produce the 110-kD polypeptide antigen, EgoR1 digested DNA from *Borrelia burgdorferi* was ligated into the dephosphorylated vector pWR590 and transformed into *Escherichia coli DH5α*. In screening the gene library, 20 clones reacted with pooled high titered sera (IFA≧1280) from dogs to this spirochete. One clone expressed a 110 kilodalton (–kD) polypeptide that reacted strongly with the high titered pooled sera from dogs with Lyme borreliosis and serum from goats immunized with *B. burgdorferi*. The 110-kD protein was expressed with and without IPTG induction, indicating the protein is not a fusion protein with β-galactosidase. The *B. burgdorferi* origin of the cloned 110-kD gene was confirmed by (1) the presence of the 110-kD gene *B. burgdorferi* and its absence in other spirochetal DNA, (2) the ability of sera from dogs, horses and humans with Lyme borreliosis to react with the recombinant 110-kD protein, and (3) the ability of the monospecific anti-recombinant 110-kD sera to recognize a 75-kD protein of *B. burgdorferi*.

Evidence that the 110-kD polypeptide of the *E. coli* A-1-24 transformant contains the same epitopes as the 75-kD antigen of *B. burgdorferi* is (1) the ability of the monospecific anti-recombinant 110-kD sera to recognize a 75-kD protein of *B. burgdorferi*, and (2) the majority of the positive sera from individuals with Lyme borreliosis that reacted with the 110-kD polypeptide in *E. coli* clone A-1-24 also reacted with the 75-kD polypeptide of *B. burgdorferi*. A possible explanation of why sera from some individuals with Lyme borreliosis reacted with the 110-kD protein and not the 75-kD antigen is simply that the 110-kD recombinant protein is produced in higher amounts. The size difference currently can not be explained but may be due to differences in post translational processing. For example, see I. G. Charles et al., PNAS USA, 86, 3554 (1989).

Immunological diagnosis of Lyme borreliosis is uncertain using available procedures. False positive IFA and ELISA reactions can occur in individuals with syphilis, relapsing fever, yaws, and pinta (L. Magnelli et al., *J. Infect. Dis.*, 156, 183 (1987)). Even by Western blot analysis, it has been shown that sera of patients with these spirochetal diseases show cross reactions to the 41-kD and 60-kD proteins of *B. burgdorferi* (R. L. Grodzicki et al., *J. Infect. Dis.*, 157, 790 (1988). Sera from some patients with autoimmune diseases such as rheumatoid arthritis and systemic lupus erythematosus have false positive reactions in *B. burgdorferi* serological tests (H. Russell et al., *J. Infect. Dis.*, 149, 465 (1984)).

The 110-kD polypeptide can be used in the diagnosis of Lyme borreliosis by standard techniques, such as those of enzyme-linked immunosorbent assays (ELISA), since a majority of individuals from three species of mammals which have clinical signs of Lyme borreliosis are capable of eliciting an antibody response to the recombinant 110-kD antigen during natural infection. False positive reactions were not observed with the 110-kD polypeptide. Sera from humans, dogs, cattle and horses with no signs of Lyme borreliosis and titers which are at background levels did not react with the 110-kD antigen on immunoblotting. Secondly, the cross-reaction of anti-110-kD sera with other spirochetes was minimal (i.e.≦10%), and hybridization of the DNA insert to DNA from other Borrelia spp. was nonexistent.

Sera collected from rabbits immunized with the 110-kD polypeptide reduced the concentration of spirochetes growing in BSK-II media in vitro. Examination of the cultures showed that in the presence of anti-110-kD polypeptide antisera, *B. burgdorferi* formed a visible aggregate at the bottom of the tube. The addition of complement or heat treatment of the sera did not significantly affect this result. These results are in agreement with the observation that virulent spirochetes are resistant to complement mediated lysis but stand in contrast to reports of complement mediated lysis of *B. burgdorferi*. These data also suggest that the gene product in *B. burgdorferi* is a surface protein since anti-110-kD sera agglutinated with bacterial cells.

Anti-110-kD sera protected mice from joint swelling following a challenge of $10^8$ *B. burgdorferi* spirochetes, but it did not significantly reduce the recovery of *B. burgdorferi* from mice. The data suggest that mice which were protected against signs of Lyme borreliosis may be infected with the spirochete. Direct injury by the spirochete has been suggested to play a role in the pathogenesis of Lyme borreliosis since the disease is treatable with antibiotics and spirochetes have been cultured and identified in ECM lesions. Since we found infection in mice with no joint swelling it appears that direct injury may not be responsible for this clinical sign.

Passive immunization using polyclonal antiserum to *B. burgdorferi* MM1 or the purified recombinant 110-kD polypeptide protected C3H/He mice from joint swelling but not from infection with *B. burgdorferi* MM1. These data support the observation that mice can be protected from signs of Lyme borreliosis with antibodies to *B. burgdorferi*. The presence of a sub-clinical infection in our studies is probably due to the large challenge inoculum ($10^8$ versus a dose of $10^4$ spirochetes used by Fikrig et al.), the route of challenge (intraperitoneally versus intradermally), the different isolates of *B. burgdorferi* used, and/or antibody titer. An inoculum of $10^8$ spirochetes, 1000 times higher than found in ticks was used for the challenge to maximize the evaluation of immunizing potential of the 110-kD polypeptide.

Immunization of mice with purified 110-kD polypeptide, followed by challenge with *B. burgdorferi* showed no evidence of Lyme disease symptoms after 14 days and no evidence of infection, upon autopsy. Thus, the 110-kD polypeptide antigen can be used as the basis for a vaccine for domestic animals and man.

To prepare a vaccine, the purified 110-kD polypeptide can be isolated as described hereinbelow, lyophilized and stabilized. The polypeptide antigen may then be adjusted to an appropriate concentration, optionally combined with a suitable vaccine adjuvant, and packaged for use. Suitable adjuvants include but are not limited to: surfactants, e.g., hexadecylamine, octadecylamine, lysolecithin, dimethyldioctadecylammonium bromide, N,N-dioctadecyl-N'-N-bis(2-hydroxyethyl-propane di-amine), methoxyhexadecylglycerol, and pluronic polyols; polanions, e.g., pyran, dextran sulfate, poly IC, polyacrylicacid, carbopol; peptides, e.g., muramyl dipeptide, dimethylglycine, tuftsin, oil emulsions, alum, and mixtures thereof. Finally, the immunogenic product may be incorporated into liposomes for use in a vaccine formulation, or may be conjugated to polysaccharides or other polymers.

The absolute weight of the polypeptide included in a given unit dosage form of vaccine can vary widely, e.g. from 5 ug-300 mg, and depends upon factors such as the age, weight and physical condition of the animal or the human subject considered for vaccination. Such factors can be readily determined by the clinician or veterinarian employing animal models or other test systems which are well known to the art. A unit dose of the vaccine is preferably administered parenterally, e.g., by subcutaneous or by intramuscular injection.

The invention will be further described by reference to the following detailed examples, wherein the *B. burgdorferi* MM1 isolate from a kidney of *Peromyscus leucopus* in Minnesota, USA, by the methods of K. Locen et al., *Proc. Soc. Exp. Biol. Med.*, 173, 300(1985). *B. burgdorferi* isolate B31, *Borrelia hermsii* (HS1), *Borrelia anserina*, and *Treponema denticola* were provided by R. C. Johnson, University of Minnesota, Minneapolis, Minn. Isolate B31 originated from the tick, *I. dammini*, from Shelter Island, N.Y., as reported by W. Burgdorfer et al., *Science*, 216, 1317 (1982). *Leptospira interrogans* serovars canicola and pommona were provided by the Veterinary Diagnostic Laboratory, University of Minnesota. *E. coli* DH5α was obtained from Bethesda Research Laboratories, Inc., Gaithersburg, Md.

Male and female CF-1 strain white mice each weighing 20 to 25 gms were obtained from Jackson Labs (Bar Harbor, Me.). Female C3H/He mice (3–4 weeks age) and New Zealand rabbits (9–12 months age) were obtained from Harlan Sprague Dawley Laboratories, Inc., Indianapolis, Ind. and Birchwood Farms (Red Wing, Minn.), respectively.

An MM1 isolate passaged three times was given in a modified BSK-II media at 34° C. Spirochetes were grown to a concentration of ca. $10^8$ viable organisms per ml for inoculation.

*T. denticola* was grown in a medium at 34° C. as described by R. M. Smibert in *The Biology of Parasitic Spirochetes*, R. C. Johnson, ed., Academic Press, N.Y. (1976). *Leptospira* were grown in a medium at 30° C., as developed by R. F. Bey et al., *Infect. Immunol.*, 19, 562 (1978). Cells were recovered by centrifugation, washed once in 10 ml of TES buffer (50 mM Tris-HCl[pH8.0], 10 mM EDTA, and 50 mM NaCl), and suspended in 5 ml of TES with 50 mg/ml of RNase A. Lysozyme was added to a final concentration of 2 mg/ml. After 20 min at 37° C., 20 ul of proteinase K (25 mg/ml) and 5 ml of 10% SDS were added. The mixture was incubated 12–15 hr at 37° C. DNA was extracted once with phenol, three times with phenol/chloroform, and then with chloroform. The aqueous phase was removed, mixed with a half volume of 7.5M ammonium acetate, and the DNA precipitated with 0.6 volume of isopropanol. The DNA precipitate was collected by a 1 min centrifugation at 12,000×g, washed thoroughly with 70% (v/v) ethanol, and resuspended in TE buffer (10 mM Tris-HCl [pH 8.0] and 1 mM EDTA).

Genomic libraries were constructed as described by T. Maniatis et al. in *Molecular Cloning: A Laboratory Manual*, Cold Spring Harbour, N.Y. (1982). *B. burgdorferi* MM1 DNA was partially digested with ECOR1 and 2–8 kb fragments were isolated on a 10–40% (w/v) sucrose gradient. DNA fragments were ligated with T4 DNA ligase (Bethesda Research Laboratories, Gaithersburg, Md.) to the plasmid vector pWR590 (L. Guo et al., *Gene*, 29, 251 (1984)) which was dephosphorylated with calf intestinal alkaline phosphatase (Promega Biotech, Madison, Wis.). Recombinant plasmids were used to transform *E. coli* DH5α and transformants were selected by growth on Luria broth (LB) plates containing 100 μg of ampicillin per ml. Colonies were transferred by replica planting to nitrocellulose filters (HATF, 0.45 μm; Millipore Corporation, Bedford, Mass.). For the induction of a fusion protein, 0.5 mM isopropyl β-D-thiogalactosidase (IPTG; Sigma Chemical Co., St. Louis, Mo.) was added to a 18 hr culture of *E. coli*, growing in LB broth and incubated for 8 hr at 37° C.

The genomic library was screened immunologically as described by R. A. Younget al., *PNAS USA*, 80, 1194 (1983). Replica membranes each containing approximately 3000 colonies were lysed by chloroform vapor for 15 min, and then treated with a buffer containing 50 mM Tris-HCl (pH 7.5), 150 mM NaCl, 5 mM $MgCl_2$, 5% non-fat dried milk (NFDM), 2 μg of DNAse, and 40 μg of lysozyme per ml overnight at room temperature with shaking. Filters were rinsed with Trissaline (50 mM Tris-HCl [pH 7.5], 150 mM NaCl) and 5% NFDM to remove any remnants of the Colonies.

Primary antibody (sera from dogs which had an IFA titer of ≧ 1280 against *B. burgdorferi*, a history of tick exposure and lameness) was diluted to 1:100 and preabsorbed with a boiled lysate of *E. coli* DH5α overnight at 4° C. The filters were incubated at 4° C. overnight with diluted and preabsorbed primary antibody, and washed 6 times with Trissaline, 5% NFDM, and 0.05% NP-40 (Sigma Chemical Company, St. Louis, Mo.). Filters were incubated with a biotin-labeled goat anti-dog IgG (H&L) diluted to 1:250 (Kirkegaard and Perry Laboratories [KPL], Gaithersburg, Md.) for 1 hr at room temperature. The filters were washed five times with Tris-saline, 5% NFDM, and 0.05% NP-40 and then reacted with a dilution of 1:500 peroxidase-labeled strepavidin (KPL) for 30 min at 37° C. After 4 additional washes, the filter was developed in 4-chloro-1-naphthol (0.6 mg/ml in phosphate-buffered saline [PBS]with 20% methanol) and 0.06% hydrogen peroxide. Positive colonies were identified by a purple appearance.

Sodium dodecyl sulfate (SDS) polyacrylamide gel electrophoresis (PAGE) was performed essentially as described by U. K. Laemmli et al., *Nature,* 227, 680 (1970). Samples for electrophoresis were prepared by washing cells twice with phosphate-buffered saline (PBS), sonicating for 5 min, and heating for 3 min in boiling water with sample buffer (0.06M Tris-HCl [pH 6.8], 3% SDS, 5% mercaptoethanol, 10% glycerol, and 0.01% bromophenol blue). Fifty micrograms of whole cell lysate protein as determined by the Bradford protein assay was loaded in each lane of a 7.5 or 10.0% acrylamide gel (M. M. Bradford, *Anal. Biochem.,* 72, 248 (1976)). Vertical electrophoresis was carried out at 25 mA for 4–6 hr.

Proteins separated in gels were transferred by semi-dry electroblotting onto nitrocellulose membranes (0.45 μm, BioRad Laboratories, Richmond, Calif.) using a Polyblot Transfer System (American Bionetics, Hayward, Calif.) in a discontinuous transfer buffer as described by the manufacturer. Transfer was carried out at 450 mA for 30 min. Cut membranes were blocked with Tris-saline (50 mM Tris-HCl [pH 7.5], 150 mM NaCl) and 5% NFDM for 1 hr at 37° C. Primary antibody was diluted to 1:100 and preabsorbed with a boiled lysate of *E. coli* DH5α. Strips were incubated at 4° C. overnight with diluted and preabsorbed primary antibody, and washed 6 times with Tris-saline, 5% NFDM, and 0.05% NP-40 (Sigma Chemical Company, St. Louis, Mo.). Strips were incubated with a biotin-labeled goat anti-dog IgG (H&L) diluted to 1:250 (Kirkegaard and Perry Laboratories [KPL]Gaithersburg, Md.) for 1 hr at room temperature. The strips were washed five times with Tris-saline, 5% NFDM, and 0.05% NP-40 and then reacted with a dilution of 1:500 peroxidase-labeled strepavidin (KPL) for 30 min at 37° C. After 4 additional washes, the strips were developed in 4-chloro-1-naphthol (0.6% mg/ml in phosphate-buffered saline [PBS]with 20% methanol) and 0.06% hydrogen peroxide.

In order to prepare rabbit antisera directed against the 110-kD protein expressed in recombinant *E. coli* or to obtain the protein for vaccination studies, the 110-kD protein band first was excised from a Coomassie-blue stained SDS gel. The excised gel slice was frozen using liquid nitrogen and pulverized with a mortar and pestle. Five to ten μg of protein and acrylamide was injected subcutaneously (s.c.) in multiple sites in each of 3 rabbits. Three weeks after the primary injection, the rabbits were reinjected s.c. with 5–10 μg of protein. Blood was collected 2 weeks following the second injection and sera were stored at –20° C.

Rabbit antisera directed against whole *B. burgdorferi* (MM1) and a non-expressing *E. coli* recombinant were also prepared. Bacteria ($10^8$ cells/ml) were washed twice and resuspended in an equal volume of 0.01M PBS. The cells were lysed with an ultrasonicator (Model W-225; Heat Systems-Ultrasonics Inc., Farmingdale, N.Y.) for 15 min and mixed with an equal volume of Freund's incomplete adjuvant (Difco Labs, Detroit, Mich.). Rabbits received two biweekly injections of 1.0 ml of material, intradermally.. Blood was collected 2 weeks following the second injection and sera were stored at –20° C.

Canine and equine sera with IFA titers of ≧ 1280 and ≧ 320, respectively, were obtained from animals which had clinical signs of Lyme borreliosis, originated from an endemic area of Lyme borreliosis and which had a history of exposure to the tick, *I. dammini.* Caprine hyperimmunized sera to *B. burgdorferi* was kindly provided by KPL. Sera from humans with Lyme borreliosis and an optical density (OD) reading of ≧ 1.00 as determined by enzyme linked immunoabsorbent assay (ELISA) was obtained from R. C. Johnson, U. of MN Medical School, Minneapolis, Minn. Normal human, dog, and horse sera were obtained from individuals with no signs or symptoms of Lyme borreliosis, or history of exposure to the tick, *I. dammini,* and an IFA titer ≧ 32 (or ELISA OD of ≧ 0.25). Mouse antisera directed against β-galactosidase was purchased from Sigma Chemical Co., St. Louis, Mo.

Mouse antisera directed against the 110-kD protein of the recombinant *E. coli* was prepared as follows.. The 110-kD protein band was excised from a Coomassie-blue stained SDS gel. The excised gel slice was frozen using liquid nitrogen and crushed with a mortar and pestle. Five to ten μg of protein in acrylamide was injected intraperitoneally. Three weeks later, the mice were reinjected with 5–10 μg of protein subcutaneously. Two weeks following the second immunization blood was collected by cardiac puncture and serum stored at –20° C.

For active immunization, 20 μg of protein is injected in Freund's complete adjuvant (Sigma Chem. Co., St. Louis, Mo.) and the immune response is boosted weekly for two weeks with the equivalent amount of protein Freund's incomplete adjuvant. All mice are then injected the *B. burgdorferi* strain MM1 spirochetes ($10^4$) intradermally, and are examined at 14 days, post-challenge.

*B. burgdorferi* was grown in BSK-II media at 34° C. for 5 days. A fixed volume (0.015, 0.03, 0.15, and 0.3 ml) of normal or immune sera was added to 3 tubes, each tube containing 3 ml of $10^8$ spirochetes/ml in BSK-II media. In 2 set of tubes the sera were heated at 56° C. for 30 min to inactivate complement; to one set of these two, guinea pig complement (Colorado Serum Company, Denver, Colo.) was added at a level of 50 units/mi. The number of viable bacteria was enumerated 24 hr later by direct microscopic count and motility.

Groups of five C3H/He mice each were injected s.c. with a fixed volume (0.1, 0.5, or 1.0 ml) of normal or immunized serum 18 hr before challenge. Challenge consisted of the i.p. injection of $10^8$ cells of the MM1 isolate in BSK-II media. Mice were maintained for 2 weeks and then sacrificed.

At 14 days postchallenge, mice were sacrificed by cervical dislocation. Kidneys and spleen were removed aseptically and forced through a three ml disposable syringe. The material was collected in 5 ml of modified BSK-II medium and a 1:10 dilution was prepared. Modified BSK-II medium was prepared by the addition of 0.15% agarose (SeaKem LE: FMC Corp., Marine Colloids Div., Rockland Me.). Cultures were examined for spirochetes by darkfield microscopy after 4 weeks of incubation at 34° C. When spirochetes were observed the animal was considered infected. Joint swelling of the hind paws of mice was determined by visual inspection. Actively immunized mice were similarly evaluated.

Example 1. Isolation of 110 KD Polypeptide from B. Burgdorferi.

A. Library construction and screening. The strategy for constructing a recombinant library containing *B. burgdorferi*

DNA fragments was to generate an EcoR1 partial restriction digest, and collect fragments of 2–8 Kb in size by sucrose gradient centrifugation. By selecting large DNA fragments, a larger proportion of clones that expressed proteins of B. burgdorferi was obtained. EcoR1 digested *B. burgdorferi* DNA (90 ng) was ligated into dephosphorylated plasmid pWR590 (10 ng), and used to transform *E. coli* DH5α. Approximately 10,000 ampicillin resistant colonies were obtained. Initial immunological screening of the library with antibodies from pooled sera of dogs with a high titer to *B. burgdorferi* revealed 200 positive clones. Upon secondary screening 20 clones reacted with the antibodies from pooled canine sera.

B. Expression of the 110-kD Polypeptide by E. coli. *B. burgdorferi* antigens expressed by recombinant clones were characterized by immunoblotting with high titered sera from dogs with Lyme borreliosis and serum from goats hyperimmunized with *B. burgdorferi.* One clone (A-1-24) expressed a 110-kD polypeptide that reacted strongly with both sera. (The insert size of this clone was 7.1 kb.) Clone A-1-24 was grown in Luria broth containing 100 μg ampicillin per ml at 37° C. A control *E. coli* clone bearing an unrelated DNA insert in the same vector did not express the 110-kD antigen. The 110-kD protein was expressed with and without IPTG. This indicated that the 110-kD protein is not expressed as a fusion protein with β-galactosidase under the control of lac Z. Verification of this was confirmed by a colony hybridization with a monoclonal antibody to β-galactosidase which only reacted with the clone following stimulation with IPTG. It appeared that *E. coli* was using a *Borrelia* promoter to produce the 110 kD protein. Southern blots of EcoR1 digested DNA of *Borrelia, Leptospira* and *Treponema* showed that the cloned fragment hybridized only with *B. burgdorferi* (MM1, B31 and G25), and with no other spirochetes.

C. Identification of the equivalent antigen in B. burgdorferi and cross-reaction of 110-kD protein to antigens found in other spirochetes. To identify the *B. burgdorferi* protein that corresponded to the cloned polypeptide, monospecific Antisera to the recombinant 110-kD protein were raised in mice. The mouse anti-110-kD sera reacted with the recombinant 110-kD protein in *E. coli* clone A-1-24 but not with *E. coli* harboring pWR590 alone. Sera from mice immunized with acrylamide excised from the 110-kD location in a lane containing *E. coli* (pWR590) lysate did not react with the 110 kD recombinant protein. Surprisingly, anti-110-kD sera recognized a protein of 75-kD in *B. burgdorferi* lysates. Since the recombinant protein does not appear to be a fusion product, the reason for the observed difference in SDS-PAGE mobility is not known.

Mouse anti-110-kD sera was used to determine if cross-reactions might exist between the recombinant 110-kD protein and antigen(s) found in other spirochetes. Antisera to the 110-kD protein reacted weakly with a 75-kD protein of *B. anserina* and *B. hermsii,* and with a 70-kD and 65-kD proteins of Leptospira species. The band of intensity of 110-kD antisera to these proteins was ten-fold less than to the 75-kD protein of *B. burgdorferi* in lanes containing equivalent amounts of bacterial lysates. Since the DNA insert encoding the 110-kD protein had no similar homology with other spirochetes, as determined by Southern blotting, it is presumed that the cross reacting proteins were unrelated.

Example 2. Immunological reactions of E. coli clone A-1-24 with sera from humans with Lyme borreliosis.

By immunoblotting, the 110-kD polypeptide antigen from clone A-1-24 reacted with 4 out of 7 sera from patients that were diagnosed by clinical symptoms and by a positive reaction with the ELISA, as show in Table 1, below

TABLE 1

Comparison of immunoblotting reactions with the *E. coli* clone expressing the 110-kD antigen to the *B.* burgdorferi lysate obtained from human and animal sera.

| | Reaction with *B. burgdorferi* lysate | |
|---|---|---|
| Serum Source | Positive[a] | Negative |
| Human | 4/7[b] | 0/9 |
| Dog | 10/10 | 0/8 |
| Horse | 5/6 | 0/11 |

[a]A reaction is scored as positive if serum reacts with two or more antigens of *B. burgdorferi.*

[b]Ratios represent the number of serum samples which react with the 110-kD protein/the total number of samples tested.

The sera which reacted with the 110-kD antigen also reacted with the 31-, 34-, and 41-kD polypeptide antigens of *B. burgdorferi* on a immunoblot. The sera which did not react with the 110-kD polypeptide, all reacted with the 41-kD polypeptide, the polypeptide recognized early in the immune response. Sera from humans with no clinical symptoms of Lyme borreliosis and an OD ≧0.25 did not react with the 110-kD polypeptide, or with the whole cell lysate of *B. burgdorferi.* One of these sera reacted with the 41-kD antigen of *B. burgdorferi* and may represent a recent spirochete infection.

Example 3. Immunological reactions of E. coli A-1-24 with sera from domestic animals with Lyme borreliosis.

By immunoblotting, the 110-kD polypeptide from clone A-1-24 was found to react with all sera from dogs with lameness, a clinical sign of Lyme borreliosis. These sera which had a high IFA titer (IFA ≧1280) also reacted with 31-, 34-, 41-, and 75-kD polypeptide antigens of *B. burgdorferi* as well as with the 110-kD polypeptide from the *E. coli* transformant. Sera from dogs with no clinical signs of Lyme borreliosis and a IFA titer ≧32 were nonreactive with the 110-kD polypeptide antigen and did not react with any antigen of *B. burgdorferi.*

The 110-kD antigen from a clone A-1-24 reacted on immunoblotting with 5 out of 6 sera from horses with clinical signs of Lyme borreliosis (Table 1). These sera had IFA titers ≧320 and positive reactions of *B. burgdorferi* on immunoblotting (data not shown). Sera from horses with no clinical signs of Lyme borreliosis and a IFA titer ≧32 were nonreactive with the 110-kD polypeptide.

Example 4. Production of immunological reagents for protection studies.

Antisera to *B. burgdorferi,* the 110-kD protein, and the *E. coli* lysate harboring pWR590 were assayed for specificity by Western blot analysis. Rabbit anti-110-kD sera and anti-*B. burgdorferi* sera diluted 1:100 and preabsorbed with a boiled lysate of *E. coli* DH5α overnight at 4° C. reacted with the recombinant 110-kD protein in *E. coli* clone A-1-24. Preabsorbed rabbit anti-*B. burgdorferi* sera and anti-*E. coli* (pWR590) sera reacted with the 60-kD antigen of *E. coli* clone A-1-24. This reaction of anti-*B. burgdorferi* sera was not unexpected since antibodies directed against the 60-kD protein of *Pseudomonas* and *Legionella* cross react with the 60-kD protein of *B. burgdorferi* as shown by K. Hansen et al., *Infect. Immunol.,* 56, 2047 (1988). The IFA titers of antiserum to *B. burgdorferi,* 110-kD recombinant protein, and *E. coli* harboring pWR590 alone were. 2560, 1280, and 320, respectively.

Example 5. In vitro effect of immune sera on B. burgdorferi.

To determine if anti-110-kD sera was as effective as anti-*B. burgdorferi* sera in reducing the number of *B. burgdorferi* in vitro, antisera to *B. burgdorferi*, the 110-kD antigen, or *E. coli* (pWR590) at levels of 0.5, 1.0, 5.0, or 10.0% were added to separate tubes containing 3 ml of viable *B. burgdorferi* ($10^8$/ml). Twenty four hours later, a concentration-dependent reduction in the number of spirochetes in solution was observed in tubes containing anti-110-kD sera or anti-*B. burgdorferi* sera, whereas in those tubes containing anti-*E. coli* sera the number of viable spirochetes did not significantly change. Anti-*B. burgdorferi* sera reduced the concentration more rapidly and to a lower level than anti-110-kD sera. This result was not unexpected since the titer of anti-110-kD sera is lower. The number of *B. burgdorferi* spirochetes in vitro, was significantly reduced depending on the amount of sera used and antigen used for immunization (ANOVA: $P<0.0001$). an antibody-facilitated aggregate of *B. burgdorferi* resulted upon addition of anti-110-kD sera or anti-*B. burgdorferi* sera to the cultures. No significant aggregate resulted from the addition of normal serum or antisera against *E. coli* (pWR590). No motility was observed with the aggregated spirochetes as determined by direct microscopy.

Example 6. In vitro effect of complement addition and heat treatment of immune sera on B. burgdorferi.

To determine the effect of complement and immune sera on the reduction in numbers of *B. burgdorferi*, heated and non-heated anti-*B. burgdorferi* sera were added to viable *B. burgdorferi* at levels of 0.5, 1.0, 5.0, and 10.0%. Both sera caused a reduction in the number of bacteria: no significant difference between the two treatments was observed. The data suggest that complement played no significant role in the destruction of bacteria. To address this, guinea pig complement was added to the heat treated immune sera. The concentration of *B. burgdorferi* in BSK-II media was reduced with the addition of this sera, however there was no significant difference with this treatment and the heated or nonheated anti-*B. burgdorferi* sera (ANOVA: $p=0.30$). Antibody-facilitated aggregation appeared to have a more significant effect than complement-mediated lysis in reducing spirochete numbers in vitro.

Example 7. Effect of immune sera on B. burgdorferi infections in mice.

To determine if immune sera protected mice from joint swelling, antisera to *B. burgdorferi*, the 110-kD polypeptide, or *E. coli* lysate was injected into C3H/He mice at levels of 0.1, 0.5, and 1.0 ml per animal preceding a challenge of $10^8$ spirochetes. As shown in Table 2, the injection of 0.1 ml of anti-*B. burgdorferi* sera protected 60% of the mice from joint swelling, while 0.5 and 1.0 ml of sera protected 100% of the mice. Amounts of 0.1, 0.5, and 1.0 ml of anti-110-kD sera protected 0, 60, and 80% of the mice from joint swelling, respectively. Anti-110-kD sera and anti-*B. burgdorferi* sera significantly reduced joint swelling when used at 0.5 and 1.0 ml per animal as compared to anti-*E. coli* sera (LOGIT: $p<0.05$).

After visual examination for joint swelling, mice were sacrificed, and organs cultured to determine if immune sera protected mice from infection with *B. burgdorferi*. Volumes of 1 and 0.5 ml of either anti-110-kD sera or anti-*B. burgdorferi* sera reduced the number of mice infected with the spirochete by 20 and 40% respectively whereas anti-*E. coli* sera did not reduce the number of infected mice (Table 3). In contrast to the prevention of joint swelling, anti-110-kD sera and anti-*B. burgdorferi* sera did not significantly reduce the recovery of *B. burgdorferi* from experimentally infected animals (LOGIT: $p=0.12$).

TABLE 2

Effect of hyperimmune sera on the protection of C3H/He mice against joint swelling.

| Antigen(s) for immunization | Volume of sera (ml) 0.1 | 0.5 | 1.0 |
|---|---|---|---|
| 110-kD protein | 5/5$^{\alpha}$ | 2/5 | 1/5 |
| *B. burgdorferi* whole cell lysate | 2/5 | 0/5 | 0/5 |
| Non-expressing *E. coli* whole cell lysate | 5/5 | 4/5 | 5/5 |
| None | ND | ND | 5/5 |

$^{\alpha}$= number of mice with joint swelling/total number of mice
ND = not determined

TABLE 3

Effect of hyperimmune sera on the experimental infection of C3H/He mice with *B. burgdorferi*.

| Antigen(s) for immunization | Volume of sera (ml) 0.1 | 0.5 | 1.0 |
|---|---|---|---|
| 110-kD protein | 5/5$^{\alpha}$ | 4/5 | 3/5 |
| *B. burgdorferi* whole cell lysate | 4/5 | 4/5 | 3/5 |
| Non-expressing *E. coli* whole cell lysate | 5/5 | 5/5 | 5/5 |
| None | ND | ND | 5/5 |

$^{\alpha}$= number of mice with infection/total number of mice
ND = not determined Example 8. Active immunization of mice.

To determine if the immune response to the 110-kD polypeptide OspA could fully prevent the clinical manifestations of disease, mice can be immunized with purified recombinant 110-kD polypeptide as described hereinabove. Control mice are immunized with adjuvant alone. An extremely strong immune response to the protein is obtained since an antibody response could be detected to a dilution of 1:64,000 by immunoblot. Groups of five mice are challenged with *B. burgdorferi* MM1 and are sacrificed at 14 days post-challenge. Histopathologic examination of the joints and heart in the animals immunized with the purified 110-kD polypeptide indicates no evidence of disease, whereas the control animals readily develop arthritis and carditis. Cultures of blood and spleen from immunized animals shows no evidence of infection, whereas all control mice are infected. Hence, the immune response that mice can generate in response to the recombinant vaccine is sufficient to protect them from subsequent infection with *B. burgdorferi* MM1.

All patents, patent applications and publications cited hereinabove are incorporated by reference herein. *E. coli* transformant A-1-24 has been deposited in the American Type Culture Collection, Rockville, Md. under accession no. ATCC 68825, under the provisions of the Budapest Treaty. The invention has been described with reference to various specific and preferred embodiments and techniques. However, it should be understood that many variations and modifications may be made while remaining within the spirit and scope of the invention.

What is claimed is:

1. A vaccine comprising an immunogenic amount of an antigenic recombinant polypeptide of about 110-kD molecular weight, as determined under reducing conditions by SDS-PAGE, wherein said polypeptide is combined with a physiologically acceptable, non-toxic liquid vehicle, which amount is effective to immunize a susceptible mammal against Lyme borreliosis, wherein the amino acid sequence of said polypeptide corresponds to the amino acid sequence of the recombinant 110-kD polypeptide produced by *E. coli* transformant ATCC 68825.

2. The vaccine of claim 1 which further comprises an effective amount of an immunological adjuvant.

3. The vaccine of claim 1 wherein the mammal is a dog, a cat, a llama, a bovine, sheep, goat or a horse.

4. The vaccine of claim 1 wherein the mammal is a human.

5. A method of protecting a susceptible mammal against Lyme borreliosis comprising administering to said mammal an effective amount of a vaccine comprising any immunogenic amount of the recombinant protein of claim 1 in combination with a physiologically-acceptable non-toxic liquid vehicle, which amount is effective to immunize the susceptible mammal against Lyme borreliosis.

6. The method of claim 5 wherein the vaccine is administered by subcutaneous or intramuscular injection.

7. The method of claim 5 wherein the vaccine is administered by oral ingestion.

8. A recombinant polypeptide of about 110-kD molecular weight, as determined by SDS-PAGE under reducing conditions, wherein the amino acid sequence of said polypeptide corresponds to the amino acid sequence of the recombinant 110-kD polypeptide produced by *E. coli* transformant ATCC 68825.

* * * * *